(12) United States Patent
Tohmeh

(10) Patent No.: US 9,226,834 B2
(45) Date of Patent: *Jan. 5, 2016

(54) SPINAL FUSION IMPLANT AND RELATED METHODS

(75) Inventor: Antoine G. Tohmeh, Spokane, WA (US)

(73) Assignee: NuVasive, Inc., San Diego, CA (US)

( * ) Notice: Subject to any disclaimer, the term of this patent is extended or adjusted under 35 U.S.C. 154(b) by 1146 days.

This patent is subject to a terminal disclaimer.

(21) Appl. No.: 13/004,474

(22) Filed: Jan. 11, 2011

(65) Prior Publication Data

US 2011/0112642 A1 May 12, 2011

Related U.S. Application Data

(63) Continuation of application No. 11/488,744, filed on Jul. 17, 2006, now Pat. No. 7,867,277.

(60) Provisional application No. 60/699,597, filed on Jul. 15, 2005.

(51) Int. Cl.
| | |
|---|---|
| *A61F 2/44* | (2006.01) |
| *A61F 2/46* | (2006.01) |
| *A61F 2/28* | (2006.01) |
| *A61F 2/30* | (2006.01) |

(52) U.S. Cl.
CPC ............... *A61F 2/4455* (2013.01); *A61F 2/46* (2013.01); *A61F 2/28* (2013.01); *A61F 2002/2817* (2013.01); *A61F 2002/2835* (2013.01); *A61F 2002/3008* (2013.01); *A61F 2002/30616* (2013.01); *A61F 2002/30785* (2013.01); *A61F 2002/30841* (2013.01); *A61F 2002/30892* (2013.01); *A61F 2002/448* (2013.01); *A61F 2002/4475* (2013.01); *A61F 2250/0098* (2013.01); *A61F 2310/00179* (2013.01)

(58) Field of Classification Search
CPC .... A61F 2/4455; A61F 2/46; A61F 2002/448
USPC ....................................... 623/17.16
See application file for complete search history.

(56) References Cited

U.S. PATENT DOCUMENTS

| | | | |
|---|---|---|---|
| 4,349,921 A | * | 9/1982 | Kuntz ........................ 623/17.16 |
| 4,834,757 A | | 5/1989 | Brantigan |
| 4,878,915 A | | 11/1989 | Brantigan |
| 5,425,772 A | | 6/1995 | Brantigan |

(Continued)

FOREIGN PATENT DOCUMENTS

| | | |
|---|---|---|
| WO | WO-0180784 A1 | 11/2001 |
| WO | WO-2005072659 A2 | 8/2005 |

*Primary Examiner* — Ellen C Hammond
(74) *Attorney, Agent, or Firm* — Jonathan Spangler; Jennifer Russell

(57) ABSTRACT

A spinal fusion implant of non-bone construction to be introduced into any variety of spinal target sites. The spinal fusion implant of the present invention includes a top surface, a bottom surface, first and second lateral sides, a proximal (posterior) end and a distal (anterior) end. The spinal fusion implant of the present invention may be used to provide temporary or permanent fixation within an orthopedic target site. To do so, the spinal fusion implant may be introduced into a disc space while locked to a surgical insertion instrument and thereafter employed in the proper orientation and released. Once deposited in the disc space, the spinal fusion implant of the present invention effects spinal fusion over time as the natural healing process integrates and binds the implant.

10 Claims, 9 Drawing Sheets

(56) References Cited

U.S. PATENT DOCUMENTS

| | | |
|---|---|---|
| 5,443,514 A | 8/1995 | Steffee |
| 5,653,762 A | 8/1997 | Pisharodi |
| 5,782,919 A | 7/1998 | Zdeblick et al. |
| 5,814,084 A | 9/1998 | Grivas et al. |
| 5,861,041 A | 1/1999 | Tienboon |
| 5,888,227 A | 3/1999 | Cottle |
| 6,033,438 A | 3/2000 | Bianchi et al. |
| 6,241,770 B1 | 6/2001 | Michelson |
| 6,264,656 B1 | 7/2001 | Michelson |
| 6,402,785 B1 | 6/2002 | Zdeblick et al. |
| 6,485,517 B1 | 11/2002 | Michelson |
| 6,537,320 B1 | 3/2003 | Michelson |
| 6,666,890 B2 | 12/2003 | Michelson |
| 6,758,849 B1 | 7/2004 | Michelson |
| 6,890,355 B2 | 5/2005 | Michelson |
| 6,923,810 B1 | 8/2005 | Michelson |
| 6,942,697 B2 | 9/2005 | Lange et al. |
| 6,974,480 B2 | 12/2005 | Messerli et al. |
| 7,022,137 B2 | 4/2006 | Michelson |
| 7,063,725 B2 | 6/2006 | Foley |
| 7,125,425 B2 | 10/2006 | Foley |
| 7,156,875 B2 | 1/2007 | Michelson |
| 7,288,093 B2 | 10/2007 | Michelson |
| 7,396,365 B2 | 7/2008 | Michelson |
| 7,455,692 B2 | 11/2008 | Michelson |
| 7,462,195 B1 | 12/2008 | Michelson |
| 7,540,882 B2 | 6/2009 | Michelson |
| 8,021,430 B2 | 9/2011 | Michelson |
| 8,444,696 B2 | 5/2013 | Michelson |
| 2001/0020186 A1 | 9/2001 | Boyce et al. |
| 2002/0082683 A1 | 6/2002 | Stinson et al. |
| 2003/0060886 A1 | 3/2003 | Van Hoeck et al. |
| 2003/0139813 A1 | 7/2003 | Messerli et al. |
| 2004/0064185 A1 | 4/2004 | Michelson |
| 2005/0096745 A1 | 5/2005 | Andre et al. |
| 2005/0143822 A1 | 6/2005 | Paul |
| 2005/0216082 A1 | 9/2005 | Wilson et al. |
| 2007/0032872 A1 | 2/2007 | Simonton |
| 2009/0062917 A1 | 3/2009 | Foley |
| 2009/0105821 A1 | 4/2009 | Michelson |
| 2009/0187246 A1 | 7/2009 | Foley |

* cited by examiner

SPINAL FUSION IMPLANT AND RELATED METHODS

CROSS REFERENCES TO RELATED APPLICATIONS

The present application is a continuation of U.S. patent application Ser. No. 11/488,744, filed on Jul. 17, 2006, which claims the benefit of priority under 35 U.S.C. §119(e) from U.S. Provisional Application Ser. No. 60/699,597, filed on Jul. 15, 2005, the entire contents of which are hereby expressly incorporated by reference into this disclosure as if set forth fully herein.

BACKGROUND OF THE INVENTION

I. Field of the Invention

The present invention relates generally to spinal surgery and, more particularly, to a device for spinal fusion comprising a spinal fusion implant of non-bone construction to be introduced into any variety of spinal target sites.

II. Discussion of the Prior Art

Currently there are nearly 500,000 lumbar and cervical spinal fusion procedures performed each year in the United States. One of the causes of back pain and disability derives from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Minimally invasive methods of performing spinal fusion have gained popularity in recent years due to the many benefits of the procedure which include diminished dissection of body tissue and lower blood loss during surgery resulting in reduced surgery time, lower post-operative pain and a quicker recovery for patients. Transforaminal lumbar interbody fusion (TLIF) procedures provide unilateral access to a desired target site. The TLIF technique involves approaching the spine in a similar manner as a posterior approach but more from the left or right of the spine through a midline incision in a patient's back. This procedure requires only one incision in the back of a patient and involves placing a fusion device into the intervertebral disc space. Introducing the intervertebral implant serves to restore the height between adjacent vertebrae ("disc height"), which reduces if not eliminates neural impingement commonly associated with a damaged or diseased disc. Distraction of the disc space with subsequent decompression of nerve roots can be accomplished by rotating a device between the adjacent vertebrae.

Current spinal fusion implants utilize either bone grafts or artificial implants to fill the intervertebral disc space. Artificial implants may be made of metal, plastic composites, ceramics, bone, or any combination thereof. Natural bone grafts have also been developed including autologous and allograft bone. Other bone grafts may include certain man-made substances including binder joining bone chips and composite bone structures.

While generally effective, the use of bone grafts presents several disadvantages. Autologous bone grafts are obtained from bone material surgically removed from the iliac crest of a patient. This method can be detrimental because it may not yield a sufficient quantity of graft material, requires additional surgery, and increases the risk of infection and blood loss. Moreover, the structural integrity at the donor site can be reduced and significant morbidity associated with harvesting the autologous bone graft may occur.

Allograft bone is obtained from cadaveric specimens, machined, and sterilized for implantation. Production of allograft bone implants may be difficult because of the inherent challenges in forecasting the receipt of cadavers. Furthermore, allograft may only provide temporary support as it is difficult to manufacture the allograft with consistent shape and strength given the differing characteristics of cadavers. Graft material usually has a smooth surface which does not provide good friction between the adjacent vertebrae and slippage of the graft may occur which can cause neural and vascular injury as well as collapse of the disc space.

A need remains for fusion implants that preserve the intradiscal space and support the vertebral column until the adjacent vertebrae are fused and still encourage bone ingrowth to achieve a solid fusion. A need also remains for implants which maximize cortical ring contact (both anteriorly and posteriorly), better facilitate self distraction of the vertebrae during insertion, avoid dural impingement and provide a better fit between anterior edge portions of vertebral endplates.

The present invention is directed at overcoming, or at least minimizing, the disadvantages of the prior art.

SUMMARY OF THE INVENTION

The present invention overcomes the drawbacks of the prior art by providing a spinal fusion implant of non-bone construction. The non-bone construction of the spinal fusion implant provides an advantage in that it is not supply limited and does not require harvesting bone from the patient (as with allograft). The present invention better facilitates cortical ring contact and fit between anterior ring portions of vertebral endplates, provides-self distraction during insertion and rotation, and avoids dural impingement.

The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant of the present invention may be provided in any number of suitable shapes and sizes depending upon the particular surgical procedure or need. The spinal fusion implant may be dimensioned for use in any part of the spine (e.g. cervical, lumbar and/or thoracic) without departing from the scope of the present invention. The implant may be dimensioned, by way of example only, having a width ranging between 8 and 14 mm, a height ranging between 8 and 18 mm, and a length ranging between 25 and 45 mm.

According to one broad aspect of the present invention, the spinal fusion implant includes a top surface, a bottom surface, lateral sides, a proximal end, and a distal end. The spinal fusion implant of the present invention may be used to provide temporary or permanent fixation along an orthopedic target site. To do so, the spinal fusion implant may be introduced into a disc space while locked to a surgical insertion instrument and thereafter manipulated in the proper orientation and released. Once deposited in the disc space, the spinal fusion implant of the present invention effects fusion over time as the natural healing process integrates and binds the implant.

The spinal fusion implant of the present invention may be provided with any number of additional features for promoting fusion, such as one or more apertures extending between the top and bottom surfaces which allow a boney bridge to form through the spinal fusion implant. The spinal implant may also be preferably equipped with one or more lateral openings which facilitate visualization at the time of implantation and at subsequent clinical evaluations.

The spinal fusion implant may also be provided with any number of suitable anti-migration features to prevent the implant from migrating or moving from the disc space after implantation. Suitable anti-migration features may include, but are not necessarily limited to, angled teeth or ridges formed along the top and bottom surfaces of the implant and/or rod elements disposed within the distal and/or proximal ends.

According to a further aspect of the present invention, the spinal fusion implant may be provided with one or more radiographic markers at the proximal and/or distal ends. These markers allow for a more detailed visualization of the implant after insertion (through radiography) and allow for a more accurate and effective placement of the implant.

According to a still further aspect of the present invention, the proximal end of the spinal fusion implant has a surface that is tapered (angled) to avoid dural impingement after implantation. Additionally, the tapered nature of the proximal surface can aid in overall fit of the spinal fusion implant within the intervertebral disc space. Significantly, the tapered proximal surface on the proximal end enables the spinal fusion implant 10 to maximize contact with the posterior portion of the cortical ring of each adjacent vertebral body.

According to a still further aspect of the present invention, the distal end of the spinal fusion implant has a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

According to a still further aspect of the present invention, the spinal fusion implant may be introduced into a spinal target site through use of any of a variety of suitable surgical instruments having the capability to engage the implant. The spinal fusion implant is capable of being used in minimally invasive surgical procedures, needing only a relatively small operative corridor for insertion.

According to a still further aspect of the present invention, once the implant has been positioned in its desired location within the intervertebral space, the user will then rotate the implant 90° such that the top and bottom surfaces face in a caudad/cephalad direction and the anti-migration features engage the vertebral bodies. Significantly, the direction of rotation is critical to ensure proper placement of the implant such that the edges of the proximal surface rest on the cortical ring of the vertebral bodies and the proximal surface does not protrude into the spinal canal. For example, if the spinal fusion implant approaches a patient's spine posteriorly from the right with the (longer) first lateral side facing caudally, then implant must be rotated in a counter-clockwise direction to achieve proper positioning.

According to a still further aspect of the present invention, one or more of the spinal fusion implants of the present invention may be used in a variety of configurations in a fusion procedure, including but not limited to (and by way of example only) unilateral, paired unilateral and bilateral.

In a unilateral configuration, a single spinal fusion implant of the present invention is inserted into an intervertebral disc space and positioned obliquely across the disc space such that the proximal and distal ends are on opposite sides of the midline of the intervertebral space.

In a paired unilateral configuration, a first spinal fusion implant is inserted into the disc space and positioned obliquely within the intervertebral space, but not necessarily directly across the midline. A second spinal fusion implant is then inserted directly adjacent to the first implant such that the implants are in a side-by-side position.

In a bilateral configuration, a first spinal fusion implant is inserted into the disc space, positioned obliquely, and disposed entirely on one side of the midline of the intervertebral space. A second spinal fusion implant is the inserted into the disc space from the mirror-image posterolateral approach such that the second spinal fusion implant occupies the portion of the intervertebral space on the opposite side of the midline from the first spinal fusion implant.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The spinal fusion implant disclosed herein boasts a variety of inventive features and components that warrant patent protection, both individually and in combination.

Figure 1:
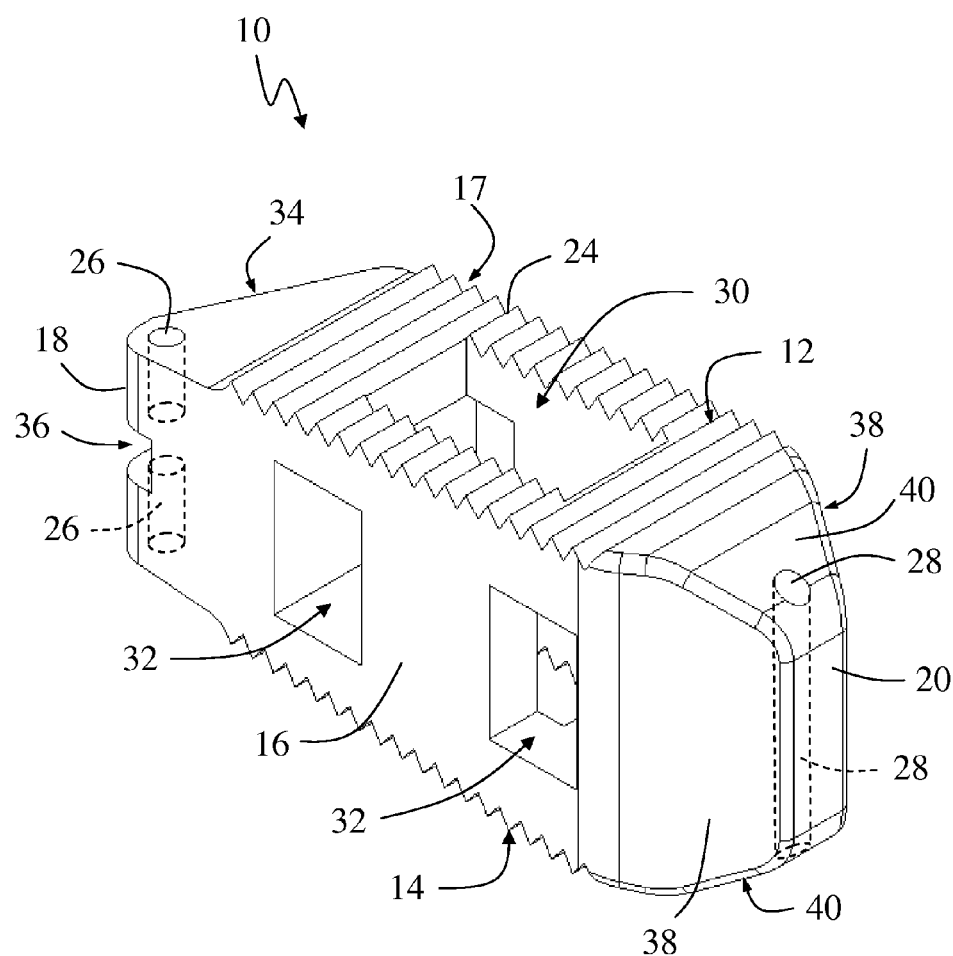
FIG. 1 is a perspective view of an example of a spinal fusion implant according to one embodiment of the present invention.

FIG. 1 illustrates a spinal fusion implant 10 according to a first broad aspect of the present invention. The spinal fusion implant 10 may be constructed of any suitable non-bone composition, including but not limited to polymer compositions (e.g. poly-ether-ether-ketone (PEEK) and/or poly-ether-ketone-ketone (PEKK)), ceramic, metal and/or any combination of polymer compositions, ceramic and metal. The spinal fusion implant 10 of the present invention may be provided in any number of shapes and sizes depending upon the particular surgical procedure or need. By way of example only, the spinal fusion implant 10 may have a width ranging between 8 and 14 mm, a height ranging between 8 and 18 mm, and a length ranging between 25 and 45 mm.

The spinal fusion implant 10 of the present invention includes a top surface 12, a bottom surface 14, first and second lateral sides 16, 17, a proximal (posterior) end 18 and a distal (anterior) end 20. The spinal fusion implant 10 of the present invention may be used to provide temporary or permanent fixation within an orthopedic target site. To do so, the spinal fusion implant 10 may be introduced into a disc space while locked to a surgical insertion instrument and thereafter employed in the proper orientation and released, as explained in further detail below. Once deposited in the disc space, the spinal fusion implant 10 of the present invention effects spinal fusion over time as the natural healing process integrates and binds the implant.

Figure 2:
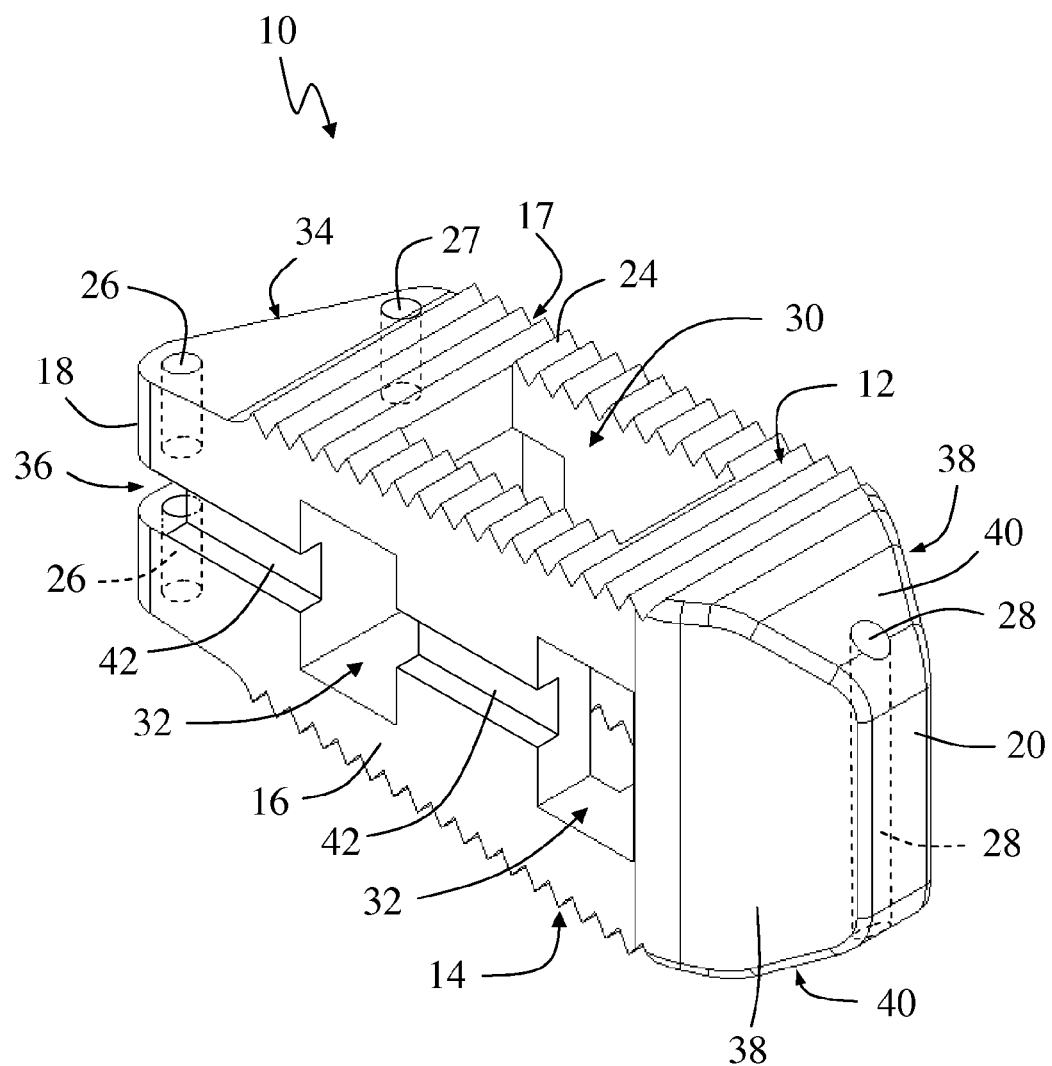
FIG. 2 is a perspective view of an example of a spinal fusion implant according to an alternative embodiment of the present invention.

FIG. 2 illustrates a spinal fusion implant 10 according to an alternative embodiment of the present invention, having slightly different (and optional) features than the spinal fusion implant of FIG. 1. Specifically, as will be discussed in greater detail below, the spinal fusion implant 10 of FIG. 2 is provided with an additional radiographic marker 27 at the proximal end and lateral recesses 42 for engagement with an insertion device.

Figure 3:
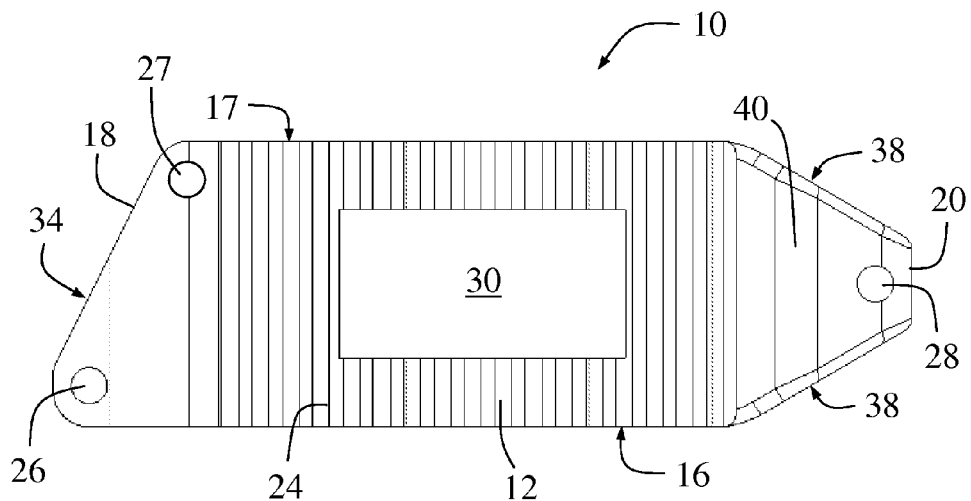
FIG. 3 is a top view of the spinal fusion implant of FIG. 2.
Figure 4:
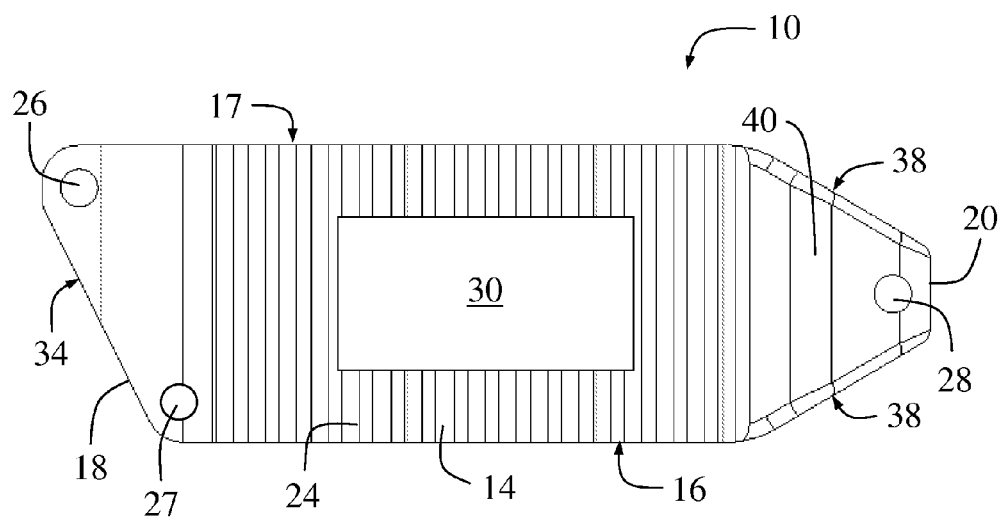
FIG. 4 is a bottom view of the spinal fusion implant of FIG. 2.
Figure 5:
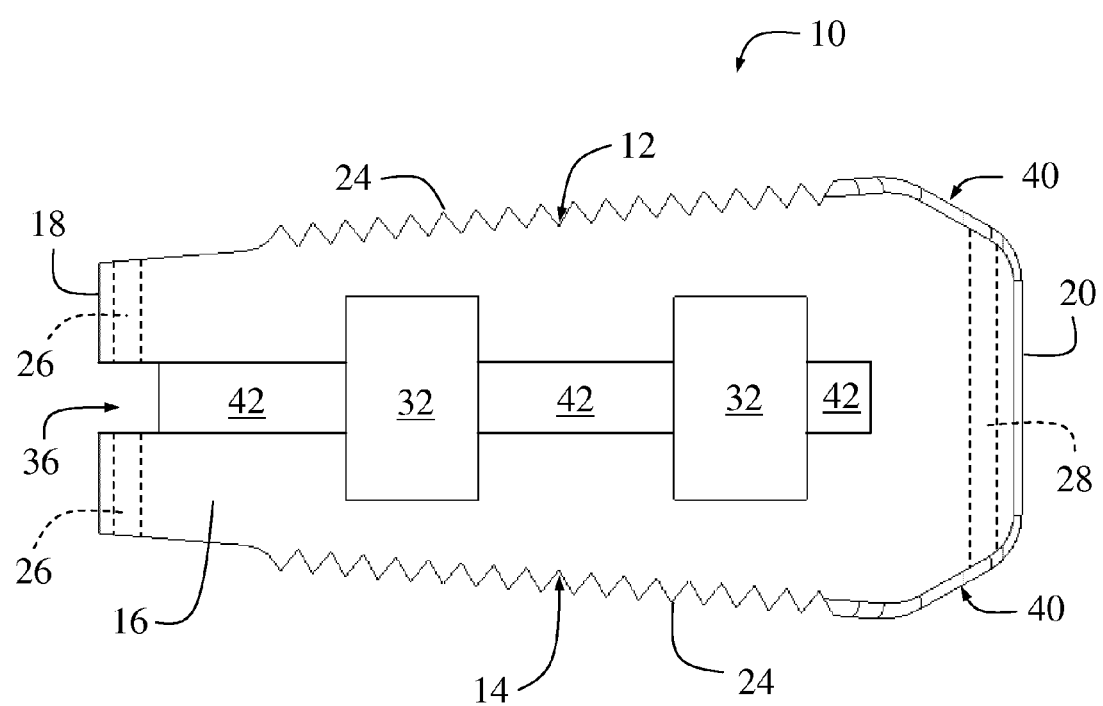
FIG. 5 is a side view of the spinal fusion implant of FIG. 2.

FIGS. 3-4 illustrate the top and bottom surfaces 12, 14, respectively, of the spinal fusion implant 10. As best depicted in FIG. 5, the top and bottom surfaces 12, 14 are not generally parallel to each other and may be angled or tapered from distal (anterior) end 20 to proximal (posterior) end 18. As such, the spinal fusion implant 10 of the present invention has a variable height along the length of the implant, as measured by the distance between the top and bottom surfaces 12, 14. By way of example only, this taper or incline may have a measured angle between 6 and 10 degrees. The practical result of this tapering is that the spinal fusion implant 10 has an anterior height that is greater than the posterior height to provide a better fit within an intervertebral disc space. It can be appreciated by one skilled in the art that the top and bottom surfaces 12, 14 may be configured in any number of suitable shapes to better match the natural contours of the vertebral end plates. For example, although the top and bottom surfaces 12, 14 are shown in the FIGS. 1-7 as being generally planar, other configurations (e.g. generally concave and/or convex) are possible.

The top and bottom surfaces 12, 14 are configured to engage the vertebral bodies adjoining the target disc space. Accordingly, the top and bottom surfaces 12, 14 each preferably include a plurality of anti-migration features designed to increase the friction between the spinal fusion implant 10 and the adjacent contacting surfaces of the vertebral bodies. Such anti-migration features may include ridges (or teeth) 24 provided along the top surface 12 and/or bottom surface 14. The friction prohibits migration of the implant 10 after insertion into the intervertebral space and during the propagation of natural bony fusion. It should be appreciated by one skilled in the art that such ridges (or teeth) 24 can be oriented in a particular direction which will stabilize the implant in several degrees of rotation during placement.

The spinal fusion implant 10 of the present invention may also be provided with one or more radiographic markers to allow for visual determination of proper implant placement. As best appreciated in FIGS. 1, 2 and 5, the proximal end 18 of implant 10 may be provided with at least a pair of radiographic markers 26, each extending between one of the top and bottom surfaces 12, 14 and the proximal engagement recess 36. Preferably, radiographic markers 26 are positioned near the intersection of first lateral side 16 and proximal surface 34. Optionally, as shown in FIG. 2, the proximal implant 18 may be further provided with a pair of radiographic markers 27, each extending between one of the top and bottom surfaces 12, 14 and the proximal engagement recess 36. Preferably, radiographic markers 27 are positioned near the intersection of second lateral side 17 and proximal surface 34. The distal end 20 may be provided with radiographic marker 28 comprising a unitary element fully extending between the top and bottom surfaces 12, 14.

The radiographic markers 26, 27, 28 may be provided in any size or shape suitable to facilitate effective and accurate visualization of implant placement. For example, the spinal fusion implant 10 shown in FIGS. 1-7 include radiographic markers 26, 27, 28 in the form of elongated cylinders extending generally perpendicularly through the implant 10 between the top and bottom surfaces 12, 14. Alternatively, radiographic markers 26, 27, 28 may include a shorter element which extends only partially from either the top surface 12 or the bottom surface 14 (that is, does not extend through the entire height of the implant 10). As a further alternative, radiographic markers 26, 27, 28 may extend at least partially (but not fully) toward either or both of top and bottom surfaces 12, 14 (that is, radiographic markers 26, 28 may be disposed completely within the body of the implant 10).

The radiographic markers 26, 28 may be manufactured from any of a variety of suitable radiopaque materials, including but not limited to a metal, ceramic, and/or polymer material, preferably having radiopaque characteristics.

The spinal fusion implant 10 includes a large aperture 30 extending between top and bottom surfaces 12, 14. FIGS. 1-4 illustrate aperture 30 extending in a vertical fashion between the top and bottom surfaces 12, 14. The aperture 30 may be provided in any number of suitable shapes, including but not limited to generally circular, generally oblong, generally triangular and/or generally rectangular (as shown by example in FIGS. 3 and 4). This single aperture 30 is an additional feature for promoting fusion between the upper and lower vertebral bodies which allow a boney bridge to form through the spinal fusion implant 10.

According to another further aspect of the present invention, this fusion may be facilitated or augmented by including osteoinductive material(s) within the aperture 30 and/or adjacent to the spinal fusion implant 10. Such osteoinductive materials may be introduced before, during, or after insertion of the spinal fusion implant 10 of the present invention, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D, L-lactide-co-glycolide) based polymers, such as those disclosed in U.S. Pat. No. 6,013,853.

FIG. 5 depicts the spinal fusion implant 10 from a side view. First and second lateral sides 16, 17 are generally parallel to one another (shown best in FIGS. 3-4). Preferably, the first lateral side 16 has a greater length than the second lateral side 17. The effect of this disparity is to cause the proximal surface 34 to be angled or tapered from the first lateral surface 16 to the second lateral surface 17. This angular surface provides an advantage by allowing an oblique positioning of the spinal fusion implant 10 within the intervertebral space, without protruding into the spinal canal, as will be explained in greater detail below. The spinal fusion implant 10 may be further provided with one or more lateral apertures 32 extending generally perpendicularly therethrough from one lateral side 16 to the other. Lateral apertures 32 function to provide visualization at the time of implantation and at subsequent clinical evaluations. Lateral apertures 32 may be provided in any of a variety of suitable shapes, including but not limited to generally circular, generally oblong, generally triangular and/or generally rectangular (shown by example in FIG. 5), or any combination thereof. Although the spinal fusion implant 10 examples shown in FIGS. 1-2 each include a pair of lateral apertures 32, the spinal implant fusion 10 may include any number of lateral apertures 10 as desired.

More specifically, based on the generally radiolucent nature of the implant 10, the lateral apertures 32 provide the ability to visualize the interior of the implant 10 during X-ray and/or other suitable imaging techniques which are undertaken from the lateral (or "side") perspective of the implant 10. If fusion has taken place, the lateral apertures 32 will provide a method for the surgeon to make follow up assessments as to the degree of fusion without any visual interference from the spinal fusion implant 10. Further, the lateral apertures 32 will provide an avenue for cellular migration to the exterior of the spinal fusion implant 10. Thus the spinal fusion implant 10 will serve as additional scaffolding for bone fusion on the exterior of the spinal fusion implant 10.

Figure 6:
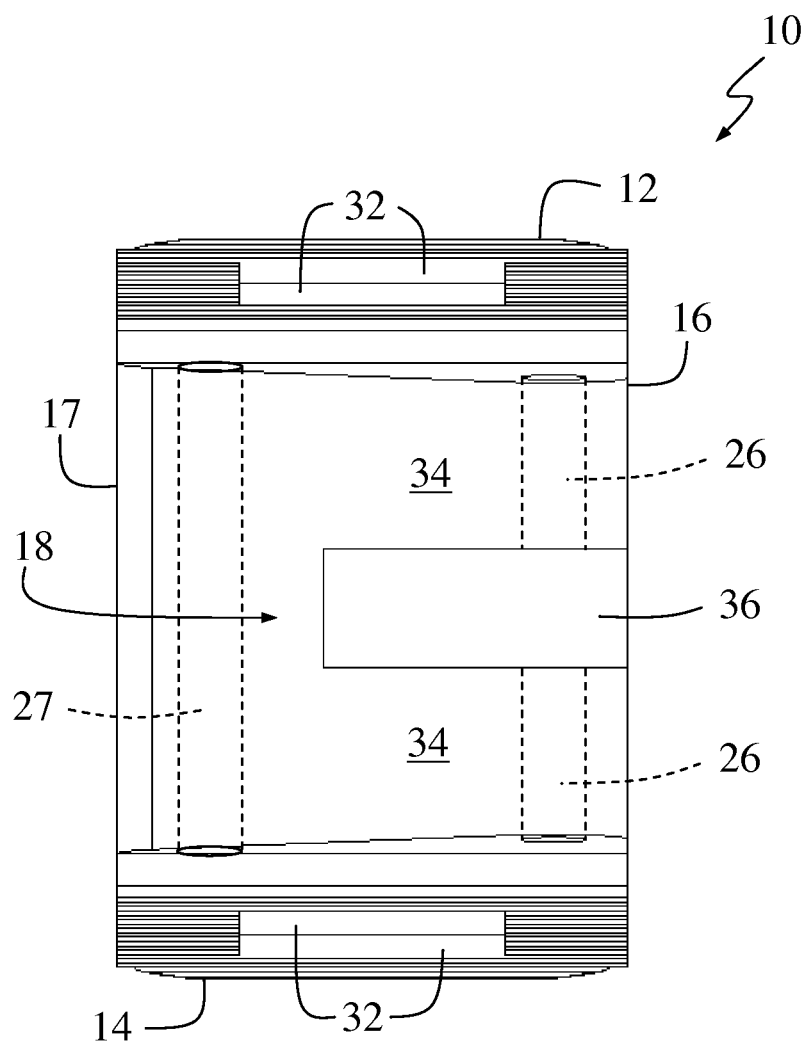
FIG. 6 is a plan view of a distal end of the spinal fusion implant of FIG. 2.

FIG. 6 illustrates the proximal end 18 of the spinal fusion implant 10 of the present invention. The proximal end 18 has a proximal surface 34 that is tapered (angled) to avoid dural impingement after insertion (as best illustrated in FIGS. 1-4). Additionally, the tapered nature of the proximal surface 34 can aid in overall fit of the spinal fusion implant 10 within the vertebral disc space. Significantly, the tapered proximal surface 34 on the proximal end 18 enables the spinal fusion implant 10 to maximize contact with the posterior portion of the cortical ring of each adjacent vertebral body. The proximal end 18 may include a proximal engagement recess 36 which extends inwardly in a generally perpendicular fashion relative to the proximal end 18. Although shown as having a generally rectangular cross-section, it will be appreciated that the proximal engagement recess 36 may be provided having any number of suitable shapes or cross-sections, including but not limited to circular or triangular. Furthermore, the proximal engagement recess 36 may extend fully or at least partially along the length of the proximal surface 34. Proximal engagement recess 36 is dimensioned to receive and engage with an insertion tool (not shown) for inserting the spinal fusion implant 10 into the intervertebral space.

Figure 7:
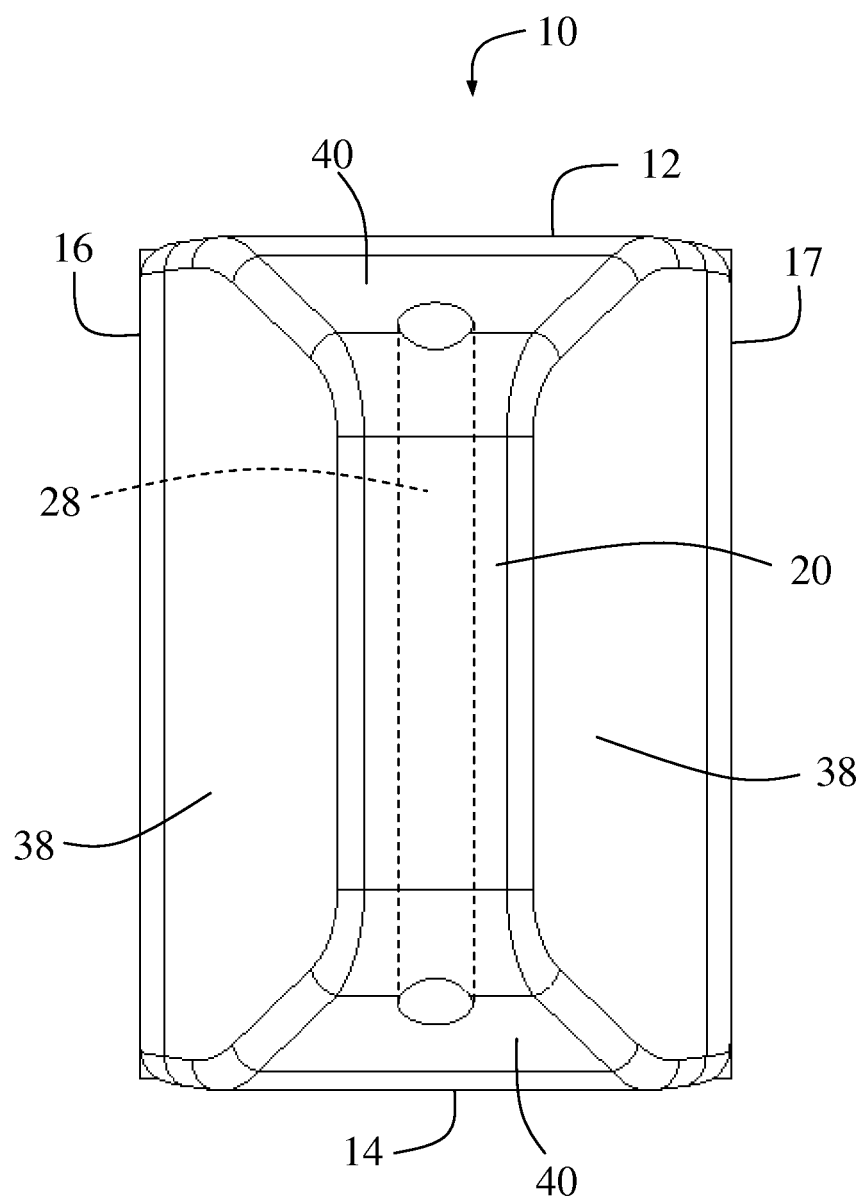
FIG. 7 is a plan view of a proximal end view of the spinal fusion implant of FIG. 2.

FIG. 7 illustrates the distal end 20 of the spinal fusion implant 10 of the present invention. The distal end 20, as best illustrated in FIGS. 1 & 2, has a conical (bullet-shaped) shape including a pair of first tapered (angled) surfaces 38 and a pair of second tapered (angled) surfaces 40. First tapered surfaces 38 extend between lateral surfaces 16, 17 and the distal end 20, and function to distract the vertebrae adjacent to the target intervertebral space during insertion of the spinal fusion implant 10. Second tapered surfaces 40 extend between top and bottom surfaces 12, 14 and the distal end 20, and function to maximize contact with the anterior portion of the cortical ring of each adjacent vertebral body. Furthermore, second tapered surfaces 40 provide for a better fit with the contour of the vertebral body endplates, allowing for a more anterior positioning of the spinal fusion implant 10 and thus advantageous utilization of the cortical rings of the vertebral bodies.

According to a broad aspect of the present invention, the spinal fusion implant 10 may be introduced into a spinal target site through use of any of a variety of suitable surgical instruments having the capability to engage the implant 10. The spinal fusion implant 10 is capable of being used in minimally invasive surgical procedures, needing only a relatively small operative corridor for insertion. By way of example only, the spinal fusion implant 10 will now be described in relation to a transforaminal lumbar interbody fusion (TLIF) technique, in which the intervertebral disc space is approached from a postero-lateral direction, however it should be understood that the spinal fusion implant 10 is capable of use in a variety of surgical procedures not described herein. After creating of this operative corridor and preparing the disc space (using techniques commonly known and used in the art), the spinal fusion implant 10 is mated to an insertion device (not shown) and advanced through the operative corridor toward the target intervertebral space. At this point the spinal fusion implant 10 is oriented with the lateral sides 16, 17 facing in a caudad/cephalad direction, for example with the first lateral side 16 facing a caudad (inferior) direction and the second lateral side 17 facing a cephalad (superior) direction. When the distal end 20 of the implant 10 reaches the intervertebral disc space, each of the pair of first tapered surfaces 38 will come into contact with one of the adjacent vertebral bodies. As the implant 10 is advanced into the intervertebral disc space, the pair of first tapered surfaces 38 will serve to distract the vertebral bodies, allowing the implant to fully enter the intervertebral space.

Since the first and second lateral sides 16, 17 are preferably provided with generally smooth surfaces, the spinal fusion implant 10 should advance with relative ease into the disc space once the adjacent vertebral bodies have been distracted. Once the implant 10 has been positioned in its desired location, the user will then rotate the implant 90° such that the top and bottom surfaces 12, 14 face in a caudad/cephalad direction and the anti-migration features 24 engage the vertebral bodies. Significantly, the direction of rotation is critical to ensure proper placement of the implant 10 such that the edges of the proximal surface 34 rest on the cortical ring of the vertebral bodies and the proximal surface 34 does not protrude into the spinal canal. For example, if the spinal fusion implant 10 approaches a patient's spine posteriorly from the right with the (longer) first lateral side 16 facing caudally, then implant 10 must be rotated in a counter-clockwise direction to achieve proper positioning. Similarly, if the spinal fusion implant 10 approaches a patient's spine posteriorly from the left side with the (longer) first lateral side 16 facing caudally, then implant 10 must be rotated in a clockwise direction to achieve proper positioning. Once the spinal fusion implant 10 has been rotated into position, the inserter may be detached and removed from the operative corridor.

Radiographic markers 26, 27, 28 may be utilized to aid in visual confirmation of proper placement of the spinal fusion implant 10. For example, when the implant 10 is properly positioned in the intervertebral space, radiographic markers 26, 27 (and others, if applicable) should be aligned such that the two (or more) markers 26, 27 positioned along the proximal end 18 appear as one when viewing a radiographic image of the spine from a lateral point of view. These markers should appear to be adjacent to the posterior portion of the cortical ring of the vertebral bodies. Likewise, the radiographic marker 28 at the distal end 20 should appear to be adjacent to the anterior portion of the cortical ring. If the proximal radiographic markers 26, 27 appear to be either misaligned or protruding into the spinal canal, or if any of the markers 26, 27, 28 appear otherwise misplaced, the surgeon may choose to reassess the placement of the implant 10. If the surgeon determines that the implant was not properly placed, then the implant 10 may be rotated in the opposite direction, repositioned, and rotated once more so that the top and bottom surfaces 12, 14 engage the vertebral bodies.

Figure 8:
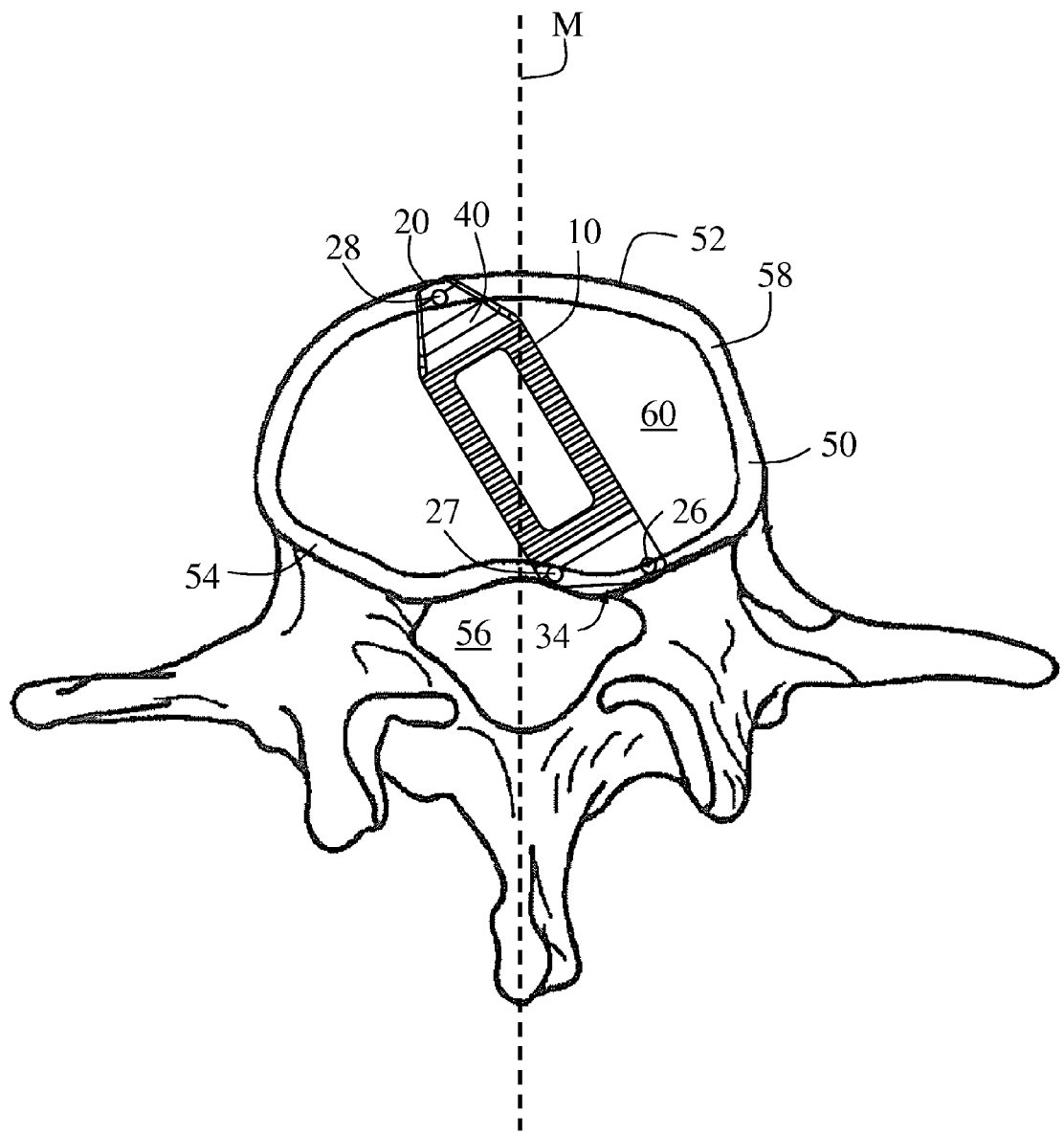
FIG. 8 is a top plan view of an example of a spinal fusion implant of the present invention inserted into an intervertebral space in a unilateral configuration.
Figure 9:
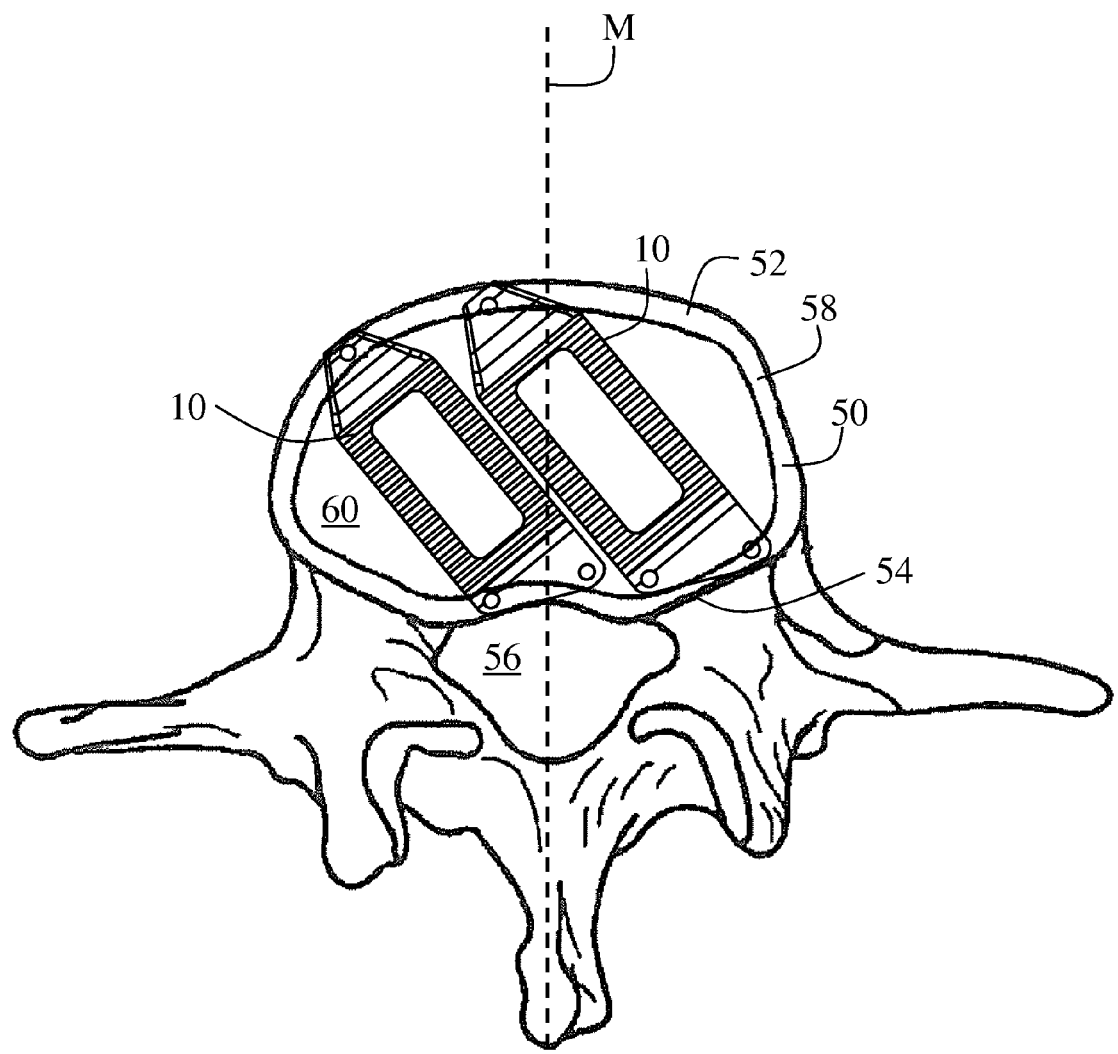
FIG. 9 is a top plan view of an example of a spinal fusion implant of the present invention inserted into an intervertebral space in a paired unilateral configuration.
Figure 10:
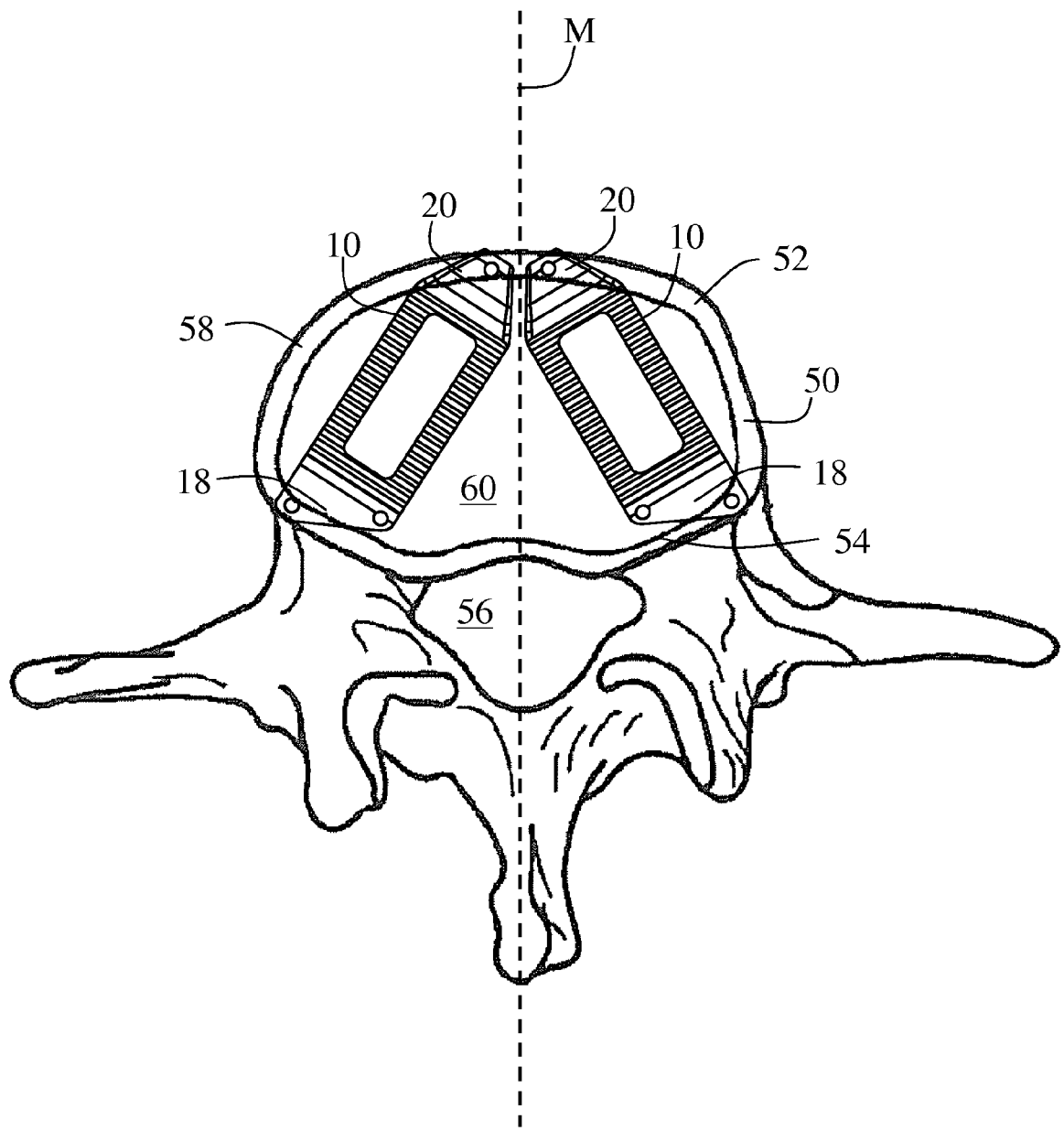
FIG. 10 is a top plan view of an example of a spinal fusion implant of the present invention inserted into an intervertebral space in a bilateral configuration.

Referring to FIGS. 8-10, one or more of the spinal fusion implant 10 of the present invention may be used in a variety of configurations in a fusion procedure, including but not limited to (and by way of example only) unilateral, paired unilateral and bilateral. For the purposes of the subsequent discussion, the intervertebral space is defined as a volume extending between adjacent vertebral bodies, having a perimeter shape that is determined by the perimeter shapes of the adjacent vertebral bodies. As shown by example in FIGS. 8-10, the intervertebral space further has a midline M defined by a line bisecting the intervertebral space in an anterior-posterior direction. Each vertebral body 50 (and consequently the intervertebral space) has a generously curved anterior portion 52 and a slightly curved (nearly planar) posterior portion 54. The posterior portions 54 of the vertebral bodies 50 and the intervertebral space lie adjacent to the spinal canal 56. Moreover, each vertebral body has a ring 58 made of stronger cortical bone surrounding an interior 60 made of cancellous bone.

Referring to FIG. 8, in a unilateral configuration a single implant 10 is inserted into an intervertebral disc space according to the procedure described above. Preferably, the implant 10 is positioned obliquely across the disc space with the implant 10 making advantageous use of the outer rings 58 of cortical bone in each of the adjacent vertebral bodies 50. The oblique positioning of the implant 10 includes positioning the implant 10 such that the distal end 20 is on one side of the midline of the intervertebral space and the proximal end 18 is on the other side of the midline. Preferably, as previously noted, when properly positioned the edge of the proximal surface 34 will interface with the cortical bone in the posterior portion 54 of the vertebral bodies 50. As a result, the proximal surface 34 will coincide with a portion of the posterior perimeter of the intervertebral space, and the implant 10 does not encroach upon the spinal canal 56. Furthermore, the distal end 20 is configured to interface with the cortical bone 58 in the anterior portion 52 of the vertebral bodies 50. The contour of each vertebral body 50 is such that the anterior portion 52 has a curvature amounting to a slightly raised lip to prevent the disc from slipping out of the space. This lip often causes problems with inserting an intervertebral implant completely within the space, and results in an inability of the implant to take advantage of the cortical bone rings 58 in the anterior portion of the disc space. Significantly, the spinal fusion implant 10 includes second tapered surfaces 40 extending between the top and bottom surfaces 12, 14 and the distal end 20. Second tapered surfaces 40 allow the distal end 40 to interface with the lip of the vertebral body 50 and therefore take full advantage of the strong cortical bone 58.

Referring to FIG. 9, in a paired unilateral configuration, a first spinal fusion implant 10 is inserted into the disc space according to the procedure described above, with one notable exception. In this configuration, the first spinal fusion implant 10 is not positioned directly across the midline M of the intervertebral space. In other words, the proximal end 18 and distal end 20 may or may not be on different sides of the midline M depending on the size and contour of the specific patient. However, the first implant 10 is still positioned obliquely within the intervertebral space such that the proximal surface 34 coincides with a proximal portion of the perimeter of the intervertebral space. Once the first implant 10 has been fully inserted (and rotated into position), a second spinal fusion implant 10 is inserted directly adjacent to the first implant 10. Upon final positioning and rotation, the second spinal fusion implant 10 should be oriented adjacent to the first spinal fusion implant 10 such that the implants 10 are in a side-by-side position.

Referring to FIG. 10, in a bilateral configuration, a first spinal fusion implant 10 is inserted into the disc space according to the procedure described above, except that the first implant 10 should be disposed entirely on one side of the midline M of the intervertebral space. Once the first implant 10 has been fully inserted (and rotated into position), a second spinal fusion implant 10 is inserted into the disc space from the minor-image postero-lateral approach. For example, if the first spinal fusion implant 10 is inserted postero-laterally from the right, then the second spinal fusion implant 10 should be inserted postero-laterally from the left. The fully inserted second spinal fusion implant 10 should occupy the portion of the intervertebral space on the opposite side of the midline from the first spinal fusion implant 10. As a result, when fully inserted the distal ends 20 of the implants 10 will be situated near each other in the anterior portion of the disc space on opposite sides of the midline M.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method of fusing adjacent first and second vertebral bodies, each vertebral body having a cancellous bone interior bounded by a cortical bone exterior wall, a generously curved anterior portion and a slightly curved posterior portion, said posterior portion adjacent to a spinal canal, and a midline extending through said anterior and posterior portions, said method comprising:

inserting a spinal fusion implant into an intervertebral space between said first and second vertebral bodies, said implant having opposing first and second engagement surfaces and opposing first and second lateral surfaces extending along a longitudinal axis, said first and second engagement surfaces including anti-migration features and being situated at generally right angles to said first and second lateral surfaces, a proximal surface extending between said first and second lateral surfaces and said first and second engagement surfaces, said first lateral surface being longer than said second lateral surface such that said proximal surface is non-perpendicular to said longitudinal axis, said spinal fusion implant further including a first radiographic marker situated between said first and second engagement surfaces and positioned such that it is centrally located near a distal surface, a second radiographic marker situated between said first and second engagement surfaces and positioned near a first proximal corner, and a third radiographic marker situated between said first and second engagement surfaces and positioned near a second proximal corner, said first proximal corner being defined by the intersecting of said first lateral surface and said proximal surface so that when viewed laterally to said longitudinal axis said second and third radiographic markers are not aligned, said spinal fusion implant being inserted into the intervertebral space such that said proximal surface is positioned on a first side of said midline and said distal surface is positioned on a second side of said midline such that said longitudinal axis is non-parallel to said midline; and viewing said spinal fusion implant radiographically from a lateral direction relative to said midline to determine if correct placement of spinal fusion implant has been achieved by observing said radiographic markers, wherein correct placement of said spinal fusion implant is accomplished when said second and third radiographic markers are aligned.

2. The method of claim 1, wherein said radiographic marker comprises radiopaque material.

3. The method of claim 2, wherein said radiopaque material comprises at least one of a metal, ceramic, and polymer.

4. The method of claim 1, wherein said anti-migration features comprise a plurality of ridges.

5. The method of claim 1, wherein at least one of said first and second engagement surfaces is generally tapered from said distal surface toward said proximal surface.

6. The method of claim 5, wherein said at least one of said first and second engagement surfaces is tapered at a measured angle ranging between 6 and 10 degrees.

7. The method of claim 1, wherein said first and second engagement surfaces are at least one of generally planar, generally convex, and generally concave.

8. The method of claim 1, said implant further comprising a central aperture extending through said implant between said first and second engagement surfaces.

9. The method of claim 1, said implant further comprising at least one lateral aperture extending through said implant between said first and second lateral surfaces.

10. The method of claim 1, wherein said implant comprises a first tapered surface extending between said distal surface and said first lateral surface and second tapered surface extending between said distal surface and said second lateral surface.

* * * * *